United States Patent
Anakwenze

(10) Patent No.: US 11,045,190 B1
(45) Date of Patent: Jun. 29, 2021

(54) SURGICAL BONE STAPLE DEVICE AND METHOD OF USE

(71) Applicant: Oke Adrian Anakwenze, San Diego, CA (US)

(72) Inventor: Oke Adrian Anakwenze, San Diego, CA (US)

( * ) Notice: Subject to any disclaimer, the term of this patent is extended or adjusted under 35 U.S.C. 154(b) by 167 days.

(21) Appl. No.: 15/973,303

(22) Filed: May 7, 2018

Related U.S. Application Data

(60) Provisional application No. 62/602,844, filed on May 8, 2017.

(51) Int. Cl.
| | |
|---|---|
| *A61B 17/068* | (2006.01) |
| *A61F 2/08* | (2006.01) |
| *A61B 17/04* | (2006.01) |
| *A61B 17/064* | (2006.01) |
| *A61B 17/00* | (2006.01) |
| *A61B 17/072* | (2006.01) |

(52) U.S. Cl.
CPC ...... *A61B 17/0682* (2013.01); *A61B 17/0401* (2013.01); *A61B 17/0483* (2013.01); *A61B 17/0642* (2013.01); *A61F 2/0811* (2013.01); *A61B 17/068* (2013.01); *A61B 17/072* (2013.01); *A61B 17/07207* (2013.01); *A61B 2017/00893* (2013.01); *A61B 2017/0409* (2013.01); *A61B 2017/0464* (2013.01); *A61B 2017/0646* (2013.01); *A61F 2002/0835* (2013.01); *A61F 2002/0852* (2013.01)

(58) Field of Classification Search
CPC .............. A61B 17/064; A61B 17/0642; A61B 17/0644; A61B 17/068; A61B 17/072; A61B 17/07207; A61B 17/00234; A61B 17/14; A61B 2017/0647; A61B 2017/00805; A61B 2017/07214; A61B 17/0682; A61B 17/0401; A61B 2017/0642; A61B 2017/10; A61B 2017/0401
USPC ....... 227/19, 175.1, 147, 119; 606/1, 72, 75, 606/104, 151, 232, 304, 219, 323, 916
See application file for complete search history.

(56) References Cited

U.S. PATENT DOCUMENTS

| | | | | | |
|---|---|---|---|---|---|
| 4,438,769 | A | * | 3/1984 | Pratt | A61B 17/0642 227/147 |
| 4,527,726 | A | * | 7/1985 | Assell | A61B 17/0682 227/121 |
| 4,592,346 | A | * | 6/1986 | Jurgutis | A61B 17/0642 411/457 |
| 4,723,540 | A | * | 2/1988 | Gilmer, Jr. | A61B 17/0642 411/456 |
| 5,328,077 | A | * | 7/1994 | Lou | A61B 17/00234 227/107 |
| 5,354,292 | A | * | 10/1994 | Braeuer | A61B 17/068 606/1 |
| 5,425,490 | A | * | 6/1995 | Goble | A61B 17/0642 227/147 |
| 5,718,706 | A | * | 2/1998 | Roger | A61B 17/0642 606/232 |

(Continued)

*Primary Examiner* — Scott A Smith
(74) *Attorney, Agent, or Firm* — Leavitt Eldredge Law Firm; Richard Eldredge; Brandon Leavitt

(57) ABSTRACT

A surgical bone staple device enables low impact installation of fasteners in bones, soft tissue and the like via a delivery tool. The staples have various support structure in the bridge area to lower pressure or healing potential. The staples could also have barbs or other features to facilitate holding the staple in place.

4 Claims, 8 Drawing Sheets

(56) References Cited

U.S. PATENT DOCUMENTS

| | | | | |
|---|---|---|---|---|
| 5,941,439 A * | 8/1999 | Kammerer | A61B 17/068 | 227/67 |
| 6,059,787 A * | 5/2000 | Allen | A61B 17/0642 | 606/75 |
| 6,193,733 B1 * | 2/2001 | Adams | A61B 17/122 | 606/151 |
| 6,554,852 B1 * | 4/2003 | Oberlander | A61B 17/0401 | 606/104 |
| 6,626,347 B2 * | 9/2003 | Ng | A61B 17/8891 | 227/119 |
| 7,341,587 B2 * | 3/2008 | Molz, IV | A61B 17/0642 | 606/279 |
| 7,749,250 B2 * | 7/2010 | Stone | A61B 17/0469 | 606/232 |
| 7,909,851 B2 * | 3/2011 | Stone | A61B 17/0482 | 606/232 |
| 8,235,995 B2 * | 8/2012 | Focht | A61B 17/068 | 606/75 |
| 8,579,909 B2 * | 11/2013 | Burkus | A61B 90/94 | 606/99 |
| 8,596,514 B2 * | 12/2013 | Miller | A61B 17/0642 | 227/175.1 |
| 8,679,123 B2 * | 3/2014 | Kinmon | A61B 17/1739 | 606/75 |
| 8,894,651 B2 * | 11/2014 | Aflatoon | A61F 2/4405 | 606/75 |
| 8,968,364 B2 * | 3/2015 | Berelsman | A61F 2/0811 | 606/232 |
| 8,986,305 B2 * | 3/2015 | Aflatoon | A61F 2/4405 | 606/75 |
| 9,017,331 B2 * | 4/2015 | Fox | A61B 17/064 | 606/75 |
| 9,451,957 B2 * | 9/2016 | Fox | A61B 17/0682 | |
| 9,585,656 B2 * | 3/2017 | Taber | A61B 17/0642 | |

* cited by examiner

SURGICAL BONE STAPLE DEVICE AND METHOD OF USE

BACKGROUND

1. Field of the Invention

The present invention relates generally to surgical bone stable devices and methods of use.

2. Description of Related Art

Bone staple devices for orthopedic surgical procedures are well known in the art. In FIGS. 1A, 1B, 1C and 1D, a common rotator cuff repair 101 is depicted. A tear 103 in tissue between the arm 107 and the shoulder 105 is cleaned by a scalpel 109. The edges of the clean tear 103 are prepared by roughing them with a tool 111. Holes are created by drill 115 and bit 113 to enable suture 117 to join the tendon 119 and the bone 107.

Conventional staple devices include having a staple frame attached to an insertion handle with a frangible joint, the handle use for placement of the staple, subsequently removed after installation by the fracture of the frangible joint. During use, the staple may be presented in an offset or angular position relative to the axis of the handle, and may be pushed into the bone or used with a low-impact tool for installation and/or separation of the frangible joint without damage or deformity to soft tissue.

It is believed that the prior art inventions do not disclose the same or similar elements as the present surgical bone staple device, nor do they present the material components in a manner contemplated or anticipated in the prior art. Great strides in the area of surgical staple devices have been made; however, many shortcomings remain and opportunities for further improvement exist.

3. Summary of the Invention

The field of minimally invasive arthroscopic surgical techniques has rapidly progressed over the last decade and continues to evolve with new techniques and procedures performed through minimally invasive techniques. Rotator cuff surgery represents one of the most common orthopedic surgeries performed. A simple description of this surgery involves identifying the tear, debriding the bone and then securing the torn tendon to the bone providing greater tuberosity. This is almost universally done with the use of suture anchors. The anchor is a screw that may be screwed within a pilot hole or impacted into the bone.

Extending out of the anchor are sutures that have to be individually passed through the tissue and then tied down to secure the tendon to bone. This process can be fairly complex depending on training, experience and tear pattern. In addition, it can be a time-consuming process passing sutures individually and tying down. The respective sutures used are heavily braided and are known to be traumatic to the tendons. Multiple needle passages can be traumatic to already torn and degenerated tissue. Proper tension/compression is not always achievable with sutures. There is also the issue of "knot security". Knots can become undone or loose.

The objective of the device provides a staple-bracket suture device. Through this device, a skilled surgeon can quickly and efficiently secure the rotator cuff to the bone in a one to two step process. The device has a unique grasper that grabs the tendon and then deploys our staple. The staple is impacted to a predetermined stop level. A pre-loaded suture in the staple is then tensioned by pulling on the tension suture attached to it. The staple will be small enough to limit excess bone and tissue loss and trauma but large enough to provide enough strength and compression. The staple may be serrated to increase further pull out strength. It may be made of metal or absorbable material with strong mechanical properties. It may also be coated with collagen scaffolds to encourage healing. This technology can be applied to all areas of surgery that use suture anchors to secure tissue to bone e.g., labral repairs, ligament repairs and reconstruction. This will greatly increase surgical time and ease. It may also lead to increased rates of healing.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1A:
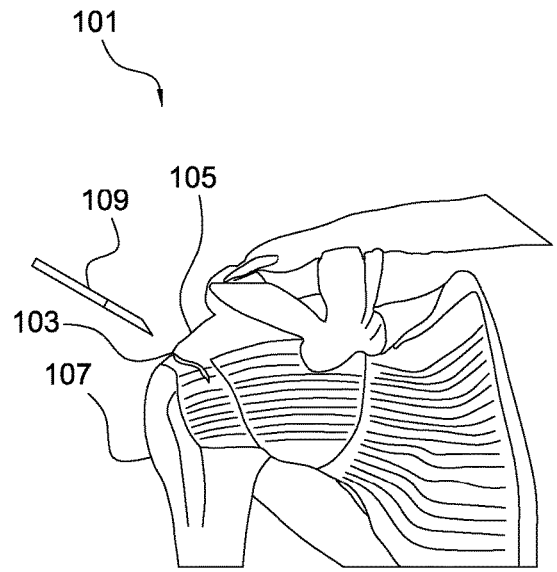
FIGS. 1A, 1B, 1C and 1D are front views of the common repair of a rotator cuff injury.
Figure 1B:
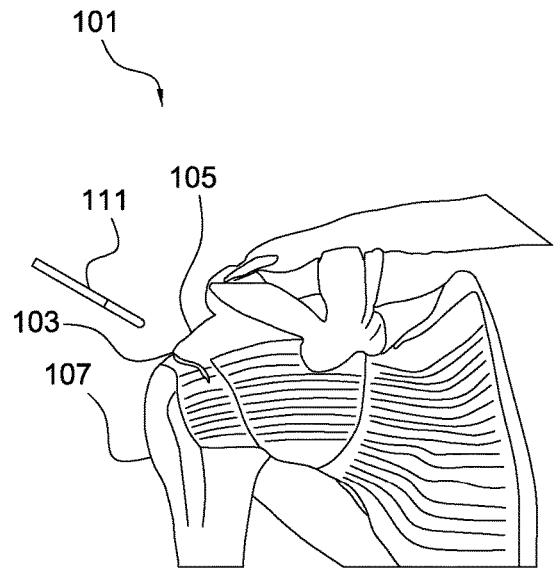
Figure 1C:
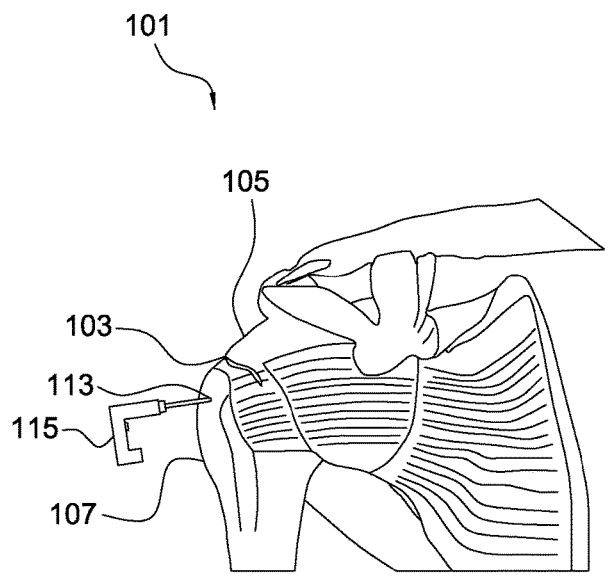
Figure 1D:
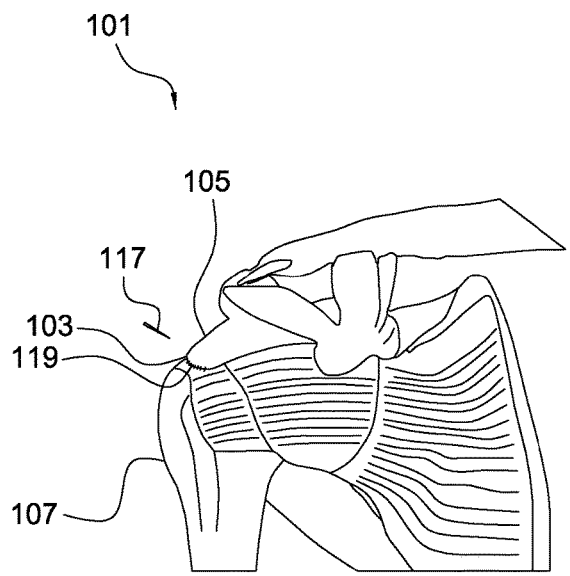

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional bone staples. Specifically, the invention of the present application provides a non-invasive and efficient method of joining ruptured tissue or bone to facilitate their healing. This and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Referring now to the drawings wherein like reference characters identify corresponding or similar elements throughout the several views, FIGS. 2-11 depict several embodiments of the invention of the application. It should be understood that the embodiments discussed herein are substantially similar in form and function and share one or more of the features discussed in each embodiment although the features may not be shown specifically with reference to the particular embodiment.

Figure 2A:
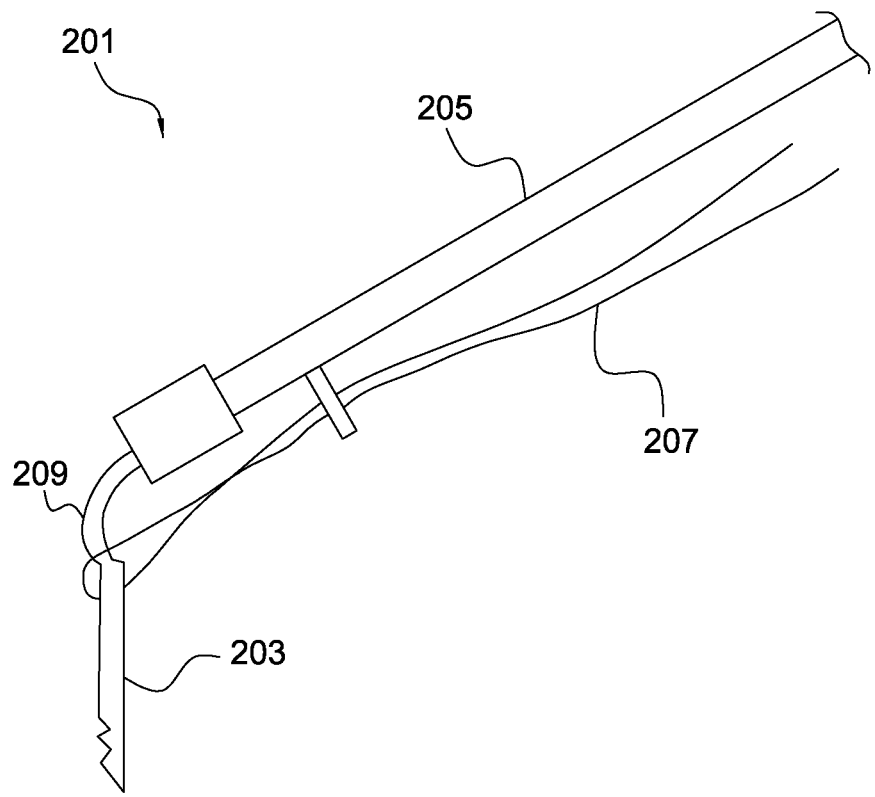
FIG. 2A is a side view of an embodiment of a frangible bone staple device in accordance with a preferred embodiment of the present application.

FIG. 2A depicts a side view of a bone staple device as exemplified by this disclosure, it is utilized by attaching soft tissues to bone without using surgical anchors, allowing a surgeon to institute placement of a fastener to retain the soft tissue on an underlying bone with minimal damage to the soft tissue or the bone. Several embodiments of the bone staple device are contained within this disclosure. It is contemplated that the invention of the present application could be used in any manner where two bodies are to be joined together and not limited to the repair of rotator cuffs, tendons, muscles or the like.

Figure 2B:
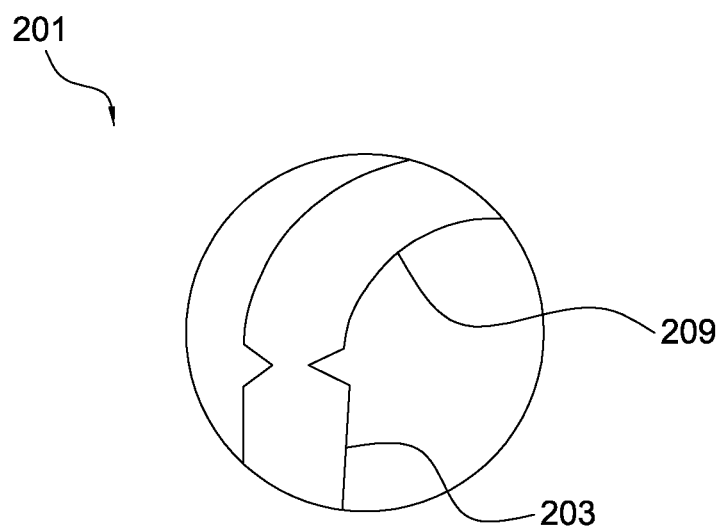
FIG. 2B is an isolation view of a frangible connection between the guide handle and a first embodiment of a surgical staple of FIG. 2A.

There are multiple types of surgical application tools—one being a handle 205 with an attachment for an individual staple 203 defining a staple and a neck extension 209 fitted within the handle 205 to deliver a single staple by a surgeon, the staple being pushed into the bone through a segment of soft tissue, the neck extension 209 defining a frangible joint as shown in FIG. 2B, wherein the staple 203 is separated from the neck extension 209, leaving the staple 203 as deployed and removing the neck extension 209 to be discarded. The handle 205 has a suture loop 207 which can be used to retain a suture which has been inserted upon the staple 203, the suture loop being held taut until such time as it is placed in its desired location. This embodiment as shown in FIG. 2A, depicts the free suture 207 looped around the staple 203 for later attachment to soft tissue to be tied and secured to the implanted staple. This staple 203 indicates barb placement on at least one of the legs of a staple 203.

Figure 3:
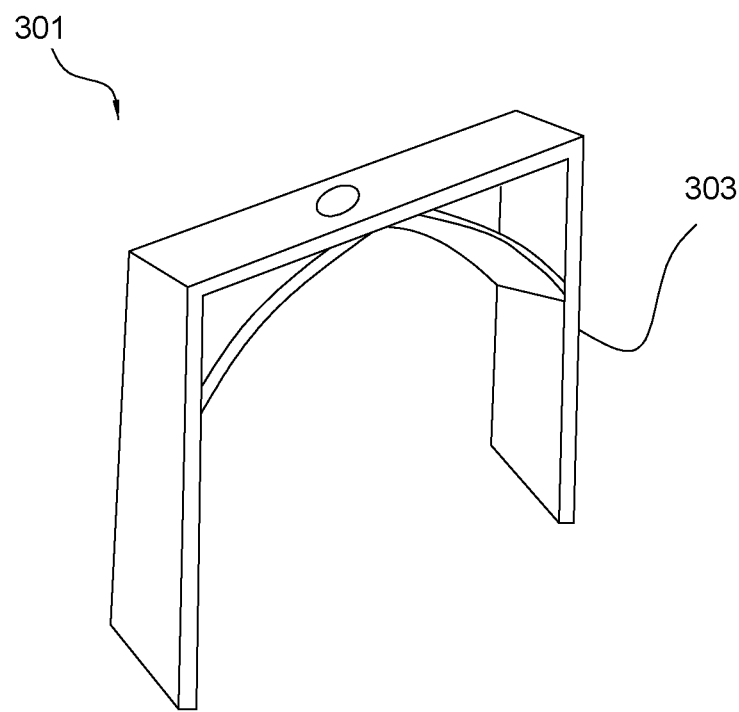
FIG. 3 is a perspective view of an alternative embodiment of a bone staple with a preset depth stop member.

An alternative embodiment 301 of staple 203 is shown in FIG. 3 which indicates the staple having a depth stop 303 to limit the depth at which the staple may be set within the bone.

Figure 4:
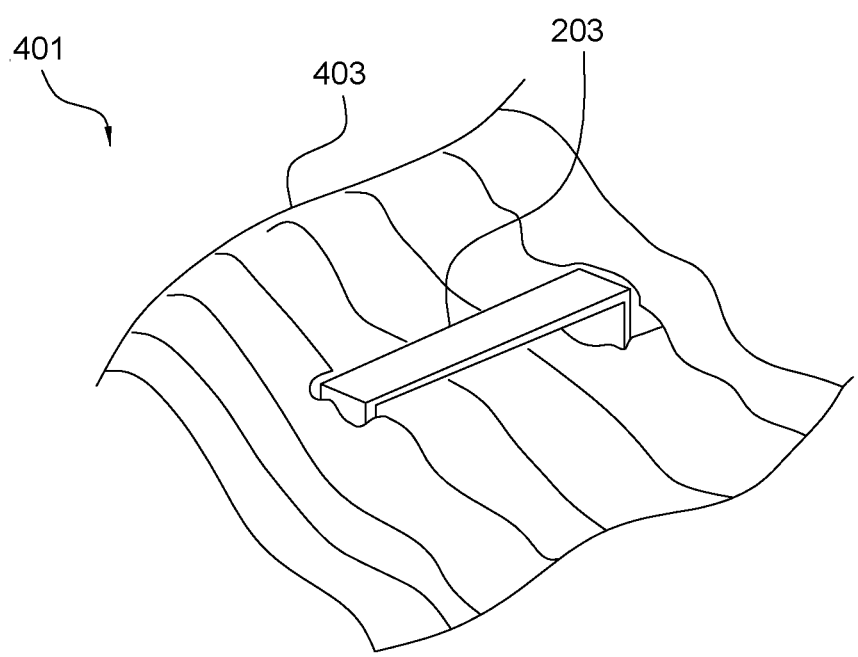
FIG. 4 is a perspective view of the bone staple of FIG. 3 used with a biologic binding material.

An alternative embodiment 401 of staple 203 is shown in FIG. 4 which would indicate a biologic material 403 or other bio-compatible material that does not impair tissue growth to provide additional cushion and a better healing environment to the staple 203.

Figure 5:
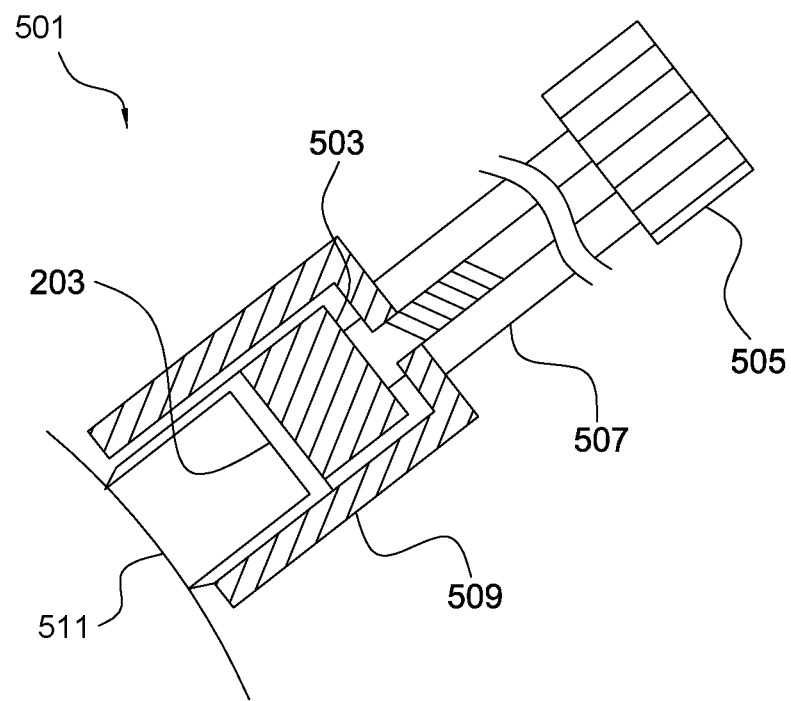
FIG. 5 is a cross-sectional side view of an alternative embodiment of a rotatable bone staple device.

FIG. 5 shows a second staple implant mechanism 501 defining a staple receiver 509, a staple push member 503 having a staple contact surface engaging the upper bridge of a two pronged staple, the rear surface connecting a threaded rod 507 which exits a rear portion of the staple receive and is connected to an expanded screw knob 505, wherein the staple is forcibly deployed from the staple receiver into the target tissue 511 by rotation of the expanded screw knob 505 advancing the staple 203 outward from the staple receiver 509.

Figure 6:
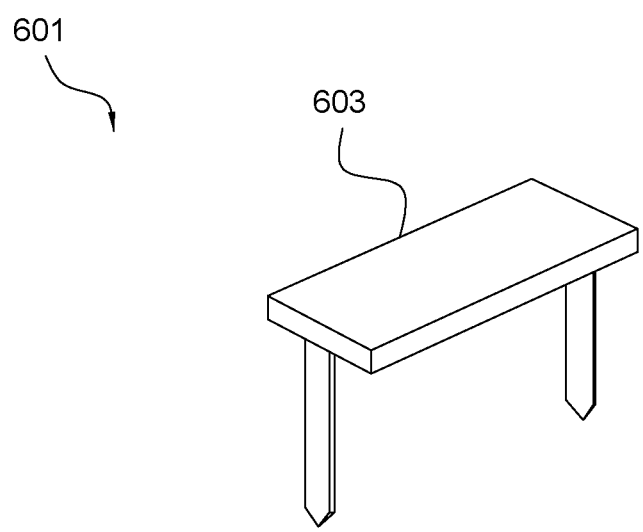
FIG. 6 is perspective view of an alternative embodiment of a bone staple with a broad connecting member.
Figure 7:
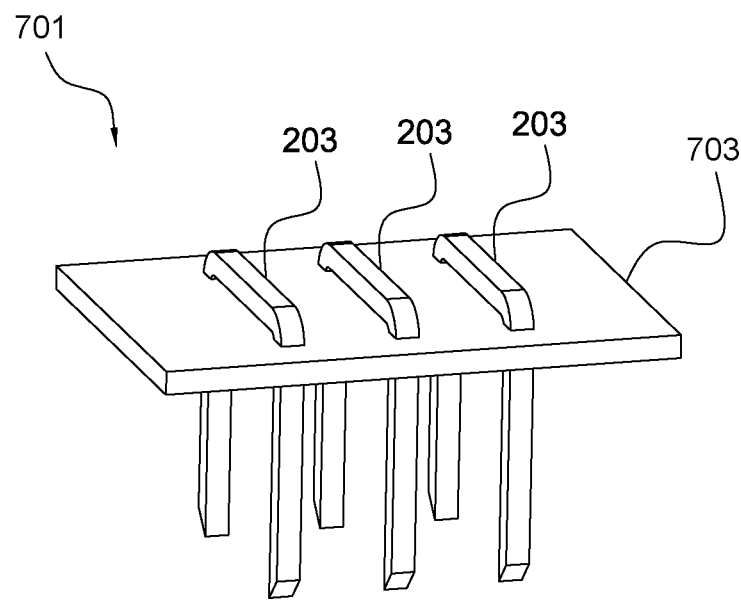
FIG. 7 is a perspective view of an alternative embodiment of a multiple bone staple assembly.

FIG. 6 shows a two pronged staple 601 with an expanded width bridge 603 to lessen the force of the bridge 603 against underlying soft tissue and to spread the force of the bridge over a greater area to reduce the risk of tearing or staple penetration through the soft tissue. FIG. 7 shows a plurality of staples 203 inserted within a bone in multiple pre-set rows or lines by engineering an expandable unit that deploys the plurality of staples in a sheet 703 when covering a larger repair site.

Figure 8:
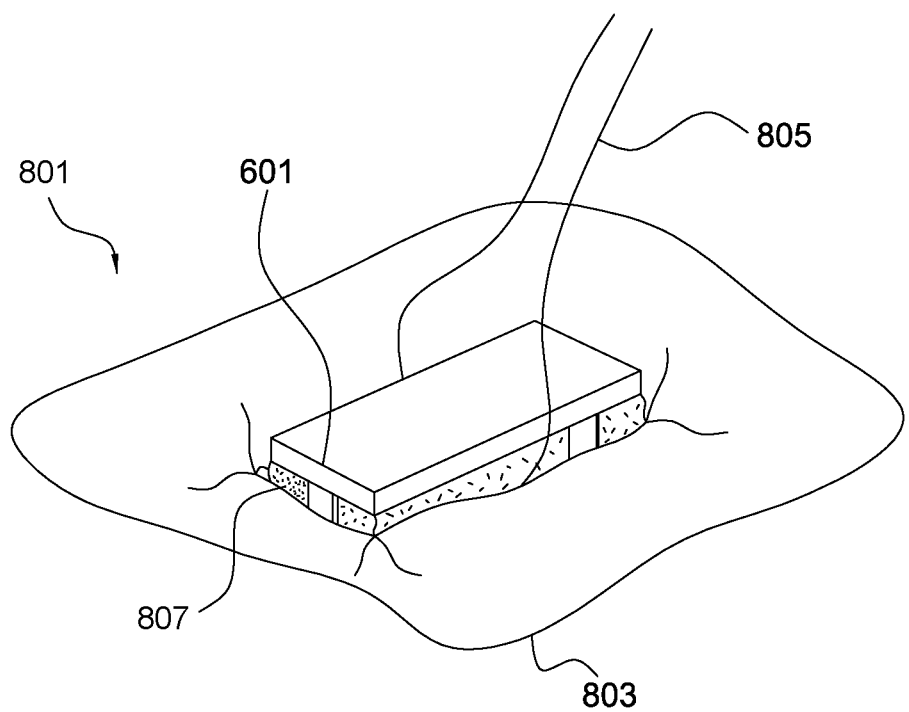
FIG. 8 is a perspective view of the multiple bone staple of FIG. 7 using a compressible structure to provide light compression to the soft tissue structures beneath the compressible structure.

FIG. 8 is a rendering of a staple 601 providing a lower biocompatible material 807 under the bridge of the staple 601 for cushion to the tissue 803, for additional tensile strength added to the staple or suture 805 being held by the staple. It may be a metallic material, absorbable material or utilize a high tensile strength suture to defray pressure to the suture and bound materials.

Figure 9:
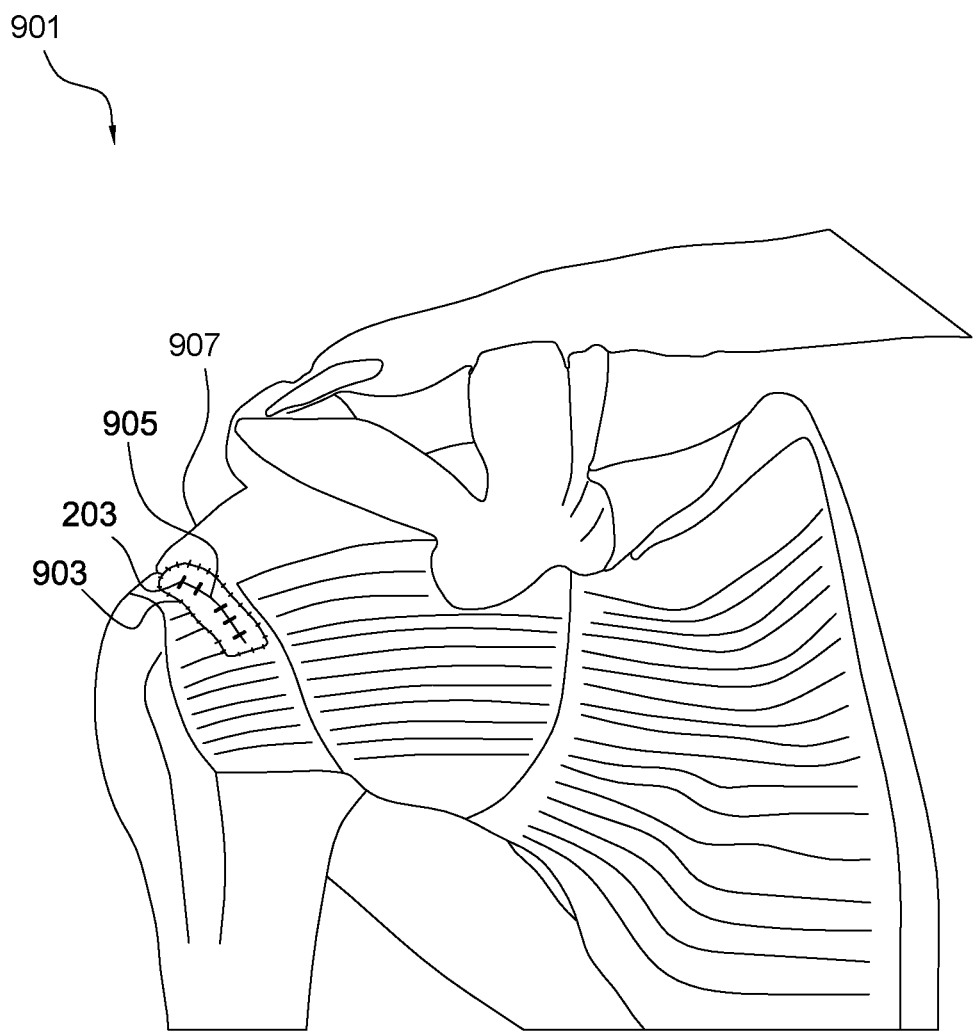
FIG. 9 is a bone staple used in conjunction with a graft tissue allowing contemporaneous attachment of the bone staple and the graft tissue over the soft tissue repair site.

FIG. 9 is a representation of a plurality of sutures 903 affixing a segment of graft tissue for severe injuries, the graft tissue being harvested from the patient, a cadaver or made of synthetic binding material on the back table, providing easier insertion of the staples 203 along line 905 within the graft tissue contemporaneously, with the graft tissue being stabilized for further suturing or further surgical use at the repair site 907.

Figure 10:
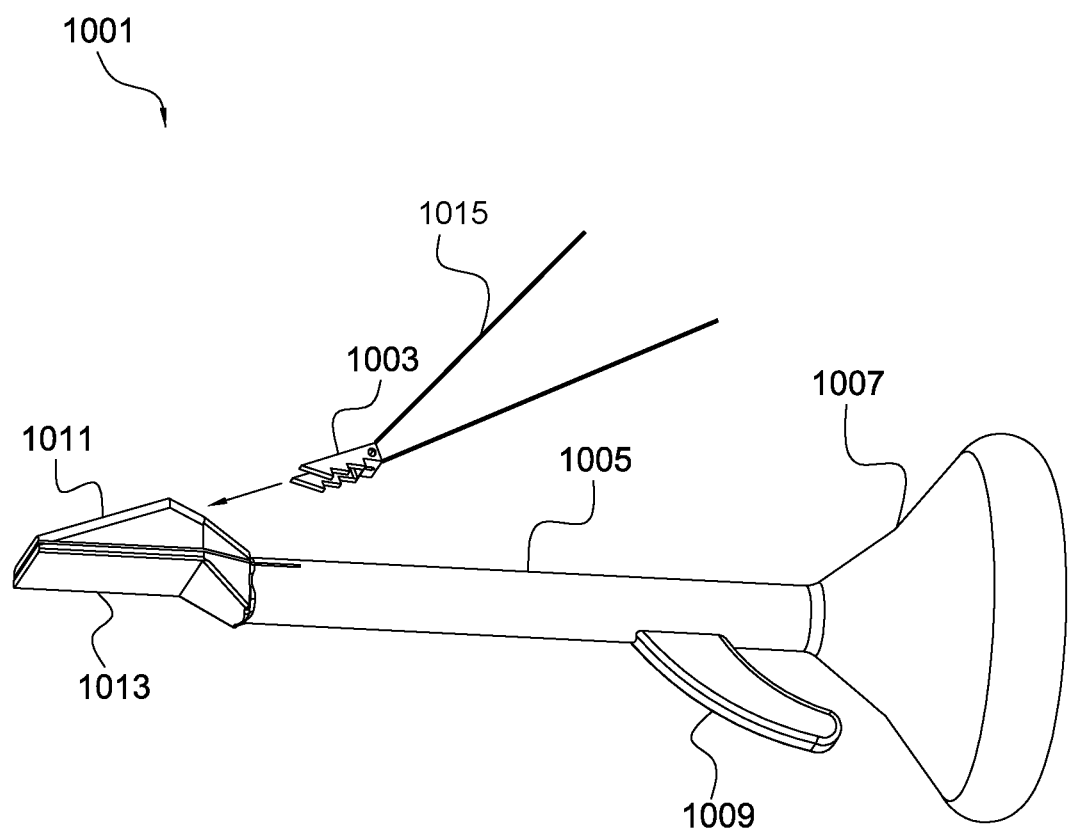
FIG. 10 is a perspective view of an embodiment of a bone staple application tool.

FIG. 10 demonstrates an alternative embodiment of the tool 201 where a staple 1003 with a loose suture loop 1015 is placed in a staple bracket 1011 that is supported by a bottom grip 1013. The staple bracket 1011 is attached to the end of a shaft 1005 having a knob handle 1007 at the opposite end and a trigger handle 1009 attached to the shaft 1005 near the knob handle 1007.

Figure 11:
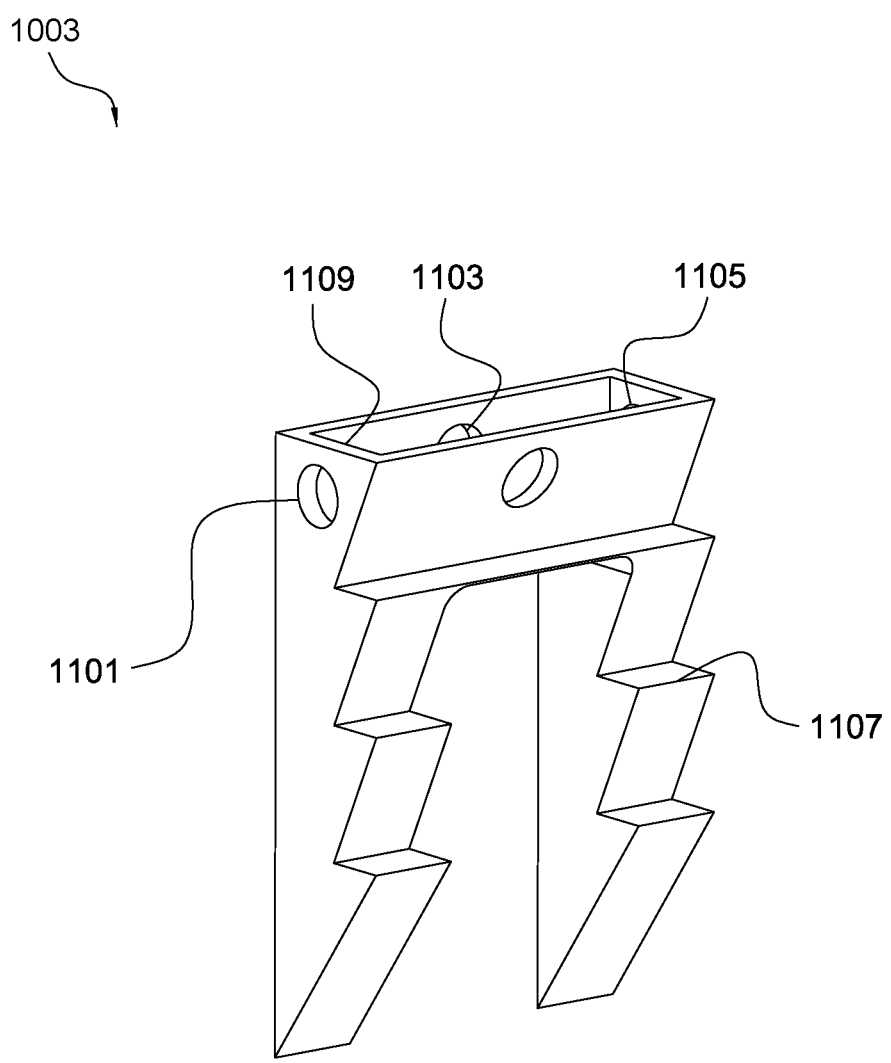
FIG. 11 is perspective view and an alternative embodiment of a bone staple.

FIG. 11 is a representation of an alternative embodiment of a staple. Embodiment 1003 including a body with a pocket 1105 having a first hole 1103 passing through two opposing sides thereof and a second hole 1101 passing though the other two opposing sides thereof. The first hole 1103 and second hole 1101 enable sutures or materials to be attached the staple 1003. The body having two prongs each with at least one barb 1107 thereon.

The bone staple devices shown are merely representative of several variations and embodiment of the staples. It is not the intent to limit the scope of the staples and instruments used to insert the staples into the tissue, nor to limit the use of the staples to rotator cuff repairs. It is ideal for rotator cuff repairs, but surgeons may choose to use the staples for other soft tissue and other bone attachments. The staples are also not limited to a two prong embodiment and may utilize one staple leg or a plurality of staple legs, with or without barbs, an in configurations not necessarily linear, including a triangular configuration, a square configuration or a polygon, with more than one bridge between the staple legs or in a geometrical design suitable for the tissue repairs. The staples may be deployed by other apparatuses, although a hard contact implement is not recommended due to the risk of penetration of the soft tissue, deformity or damage to the soft tissue or bone. The staples may be made of metal, plastic, nytinol or other biocompatible and bioabsorbable material use in bone implant devices. Although the embodiments of the have been described and shown above, it will be appreciated by those skilled in the art that numerous modifications may be made therein without departing from the scope of the invention as herein described.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A surgical bone staple device comprising:
   a shaft extending from a first end and a second end;
   a knob handle secured to the first end;
   a staple bracket secured to the second end; and
   a staple configured to engage with the staple bracket, the staple having:
   a body having at least two prongs attached via a bridge;
   the bridge forming a pocket with peripheral sidewalls;
   a hole extending through the peripheral sidewalls;
   the at least two prongs having a plurality of barbs.
2. The device of claim 1 wherein the shaft has a trigger handle attached thereto near the knob handle.
3. The device of claim 1 wherein a suture loop is attached to the staple.
4. The device of claim 1 wherein the staple is placed in bone, tendon, and muscle.

* * * * *